(12) United States Patent
Marx et al.

(10) Patent No.: US 8,486,923 B2
(45) Date of Patent: *Jul. 16, 2013

(54) USE OF THE COMBINATION OF CICLESONIDE AND ANTIHISTAMINES FOR THE TREATMENT OF ALLERGIC RHINITIS

(75) Inventors: Degenhard Marx, Moos (DE); Helgart Müller, Radolfzell (DE)

(73) Assignee: Takeda GmbH, Constance (DE)

( * ) Notice: Subject to any disclaimer, the term of this patent is extended or adjusted under 35 U.S.C. 154(b) by 22 days.

This patent is subject to a terminal disclaimer.

(21) Appl. No.: 12/973,414

(22) Filed: Dec. 20, 2010

(65) Prior Publication Data

US 2011/0092471 A1    Apr. 21, 2011

Related U.S. Application Data

(63) Continuation of application No. 10/524,821, filed as application No. PCT/EP03/09622 on Aug. 29, 2003, now Pat. No. 7,879,832.

(30) Foreign Application Priority Data

Aug. 30, 2002 (EP) ..................... 02019406

(51) Int. Cl.
*A01N 45/00* (2006.01)
*A61K 31/56* (2006.01)

(52) U.S. Cl.
USPC ....................................... 514/171

(58) Field of Classification Search
None
See application file for complete search history.

(56) References Cited

U.S. PATENT DOCUMENTS

| | | | |
|---|---|---|---|
| 3,326,924 A | 6/1967 | Villani | |
| 3,813,384 A | 5/1974 | Vogelsang et al. | |
| 4,369,184 A | 1/1983 | Stokbroekx et al. | |
| 5,164,194 A | 11/1992 | Hettche | |
| 5,482,934 A | 1/1996 | Calatayud et al. | |
| 5,733,901 A | 3/1998 | Gutterer | |
| 6,264,935 B1 | 7/2001 | Chastaing et al. | |
| 6,297,227 B1 | 10/2001 | Johnson | |
| 6,767,901 B1 | 7/2004 | Nagano et al. | |
| 7,022,687 B1 | 4/2006 | Szelenyi et al. | |
| 2002/0061281 A1 | 5/2002 | Osbakken et al. | |
| 2002/0111495 A1 | 8/2002 | Magee et al. | |
| 2002/0115680 A1 | 8/2002 | Meissner et al. | |
| 2003/0008019 A1 | 1/2003 | Nishibe et al. | |
| 2004/0097474 A1 | 5/2004 | Cagle et al. | |
| 2004/0097486 A1 | 5/2004 | Yanni | |
| 2009/0318397 A1* | 12/2009 | Lulla et al. ............... 514/171 |

FOREIGN PATENT DOCUMENTS

| | | |
|---|---|---|
| CA | 2 387 398 A1 | 3/2002 |
| DE | 195 41 689 A1 | 5/1996 |
| EP | 0 174 726 A1 | 3/1986 |
| EP | 0 709 099 A2 | 5/1996 |
| EP | 0 780 127 A1 | 6/1997 |
| EP | 0 903 151 A1 | 3/1999 |
| EP | 1 142 565 A1 | 10/2001 |
| WO | 94/22899 A1 | 10/1994 |
| WO | 97/01337 A1 | 1/1997 |
| WO | 97/01341 A1 | 1/1997 |
| WO | 97/46243 A1 | 12/1997 |
| WO | 98/48839 A1 | 11/1998 |
| WO | 01/22955 A2 | 4/2001 |
| WO | 01/28562 A1 | 4/2001 |
| WO | 01/28563 A1 | 4/2001 |
| WO | 01/35963 A1 | 5/2001 |
| WO | 02/12235 A1 | 2/2002 |
| WO | 03/049770 A1 | 6/2003 |
| WO | 03/105856 A1 | 12/2003 |

OTHER PUBLICATIONS

Hardy et al., J Pharm Pharmacol 37: 294-297 (1985).*
Mattila, et al., "Variations among non-sedating antihistamines: are there real differences?", Eur J Clin Pharmacol, vol. 55, pp. 85-93, (1999).
Schmidt, et al., "The New Topical Steroid Ciclesonide Is Effective in the Treatment of Allergic Rhinitis", J Clin Pharmacol, vol. 39, pp. 1062-1069, (1999).
Busse, et al., "Corticosteroid-sparing Effect of Azelastine in the Management of Bronchial Asthma", Am J. Respir Crit Care Med, vol. 153, pp. 122-127, (1996).
Vippagunta, et al., Advanced Drug Delivery Reviews, 2001, vol. 48, pp. 3-26.
Application No. ORA/1/2011/PT/MUM for the revocation of Patent No. IN.218635; mailed Jan. 5, 2011.

* cited by examiner

*Primary Examiner* — James H Alstrum Acevedo
*Assistant Examiner* — Thor Nielsen
(74) *Attorney, Agent, or Firm* — Nath, Goldberg & Meyer; Sheldon M. McGee

(57) ABSTRACT

The subject matter of this application relates to the combination of ciclesonide with an antihistamine.

17 Claims, No Drawings

USE OF THE COMBINATION OF CICLESONIDE AND ANTIHISTAMINES FOR THE TREATMENT OF ALLERGIC RHINITIS

This application is a continuation application of U.S. Ser. No. 10/524,821, filed Feb. 18, 2005, which is a national phase application under 35 USC §371 of PCT/EP2003/009622, filed Aug. 29, 2003.

TECHNICAL FIELD OF THE INVENTION

The present invention is related to a novel combination of ciclesonide and antihistamines for use in drug therapy in particular in the treatment of allergic rhinitis. In particular the novel combination is administered in the form of an aqueous pharmaceutical composition that contains ciclesonide and antihistamine and having an osmotic pressure of less than 290 mOsm.

BACKGROUND ART

Allergic rhinitis is a common disorder and the number of patients is steadily increasing. The disease is caused by ambient airborne allergens, which cause an allergic inflammation within the nasal mucosa and it is often accompanied by conjunctivitis. According to the allergen, the allergic rhinitis is subdivided into seasonal allergic rhinitis (allergens like grass pollen, cedar pollen) and perennial allergic rhinitis (indoor allergens like mould, allergens from animals and house dust mite). Allergic rhinitis has a great impact on the quality of life. The patients suffer from an itchy and running nose, nasal blockage, headache and fatigue. Allergic conjunctivitis is often linked to allergic rhinitis and requires co-treatment. The major symptoms of conjunctivitis are burning and itching eyes and lacrimation. The basic mechanisms involved in this disease are the same as for allergic rhinitis.

The current treatment of allergic rhinitis is mainly focused on symptomatic relief. Oral and to a lesser extent topical antihistamines are the most widely used remedies. Oral antihistamines alleviate the histamine driven symptoms only. Allergen contact causes degranulation of mucosal mast cells and histamine is released. Histamine is responsible for the itching and sneezing and the increase in nasal secretion. Antihistamines block the binding of histamine to the histamine-H1-receptor and thereof the histamine mediated symptoms. Beside this obvious pathway, the allergens cause an eosinophilic inflammation of the nasal mucosa, which is mainly responsible for symptoms like nasal hyperreactivity, nasal blockage and the fear of the so called change of floors, which means that an untreated allergic rhinitis can develop to sinusitis and asthma bronchiale.

Treatment with glucocorticoids is currently the only one therapy, which targets the underlying allergic inflammation. To avoid systemic side effects typically for glucocorticoids, e.g. immunosuppression, reduced protein synthesis, impaired growth in children, topical treatment with glucocorticoids is the preferred way of administration.

A disadvantage of nasal steroids is the slow onset of action and the need for continuous treatment. It takes 4-6 days of continuous treatment before a symptom relief can be observed. Therefore, the patients are recommended to begin to take glucocorticoids before the pollen season starts. The slow onset of action, the need of consequent treatment and the fear of steroid induced side effects have a negative impact on the use of intranasal steroids and patient's compliance.

Other medications available for the treatment are just for symptomatic relief, for example intranasal muscarinic antagonists (ipratropium to reduce nasal secretion), adrenoreceptor agonists (xylomethazoline to reduce nasal congestion).

WO 97/01337 describes a nasal spray or nasal drops formulation comprising beclomethasone, flunisolide, triamcinolone, dexamethasone or budesonide in combination with the antihistamines levocabastine, azelastine or azatadine and sterile water.

WO 97/46243 is related to a nasal spray containing an intranasal steroid and an antihistamine.

WO 98/48839 is related to topically applicable nasal compositions comprising a therapeutically effective amount of an antiinflammatory agent and a therapeutically effective amount of at least one agent selected from the group consisting of a vasoconstrictor, a neuraminidase inhibitor, a leukotriene inhibitor, an antihistamine, an antiallergic agent, an anticholinergic agent, an anesthetic and a mucolytic agent.

WO 01/22955 is related to a novel combination of loteprednol, a so-called soft steroid with antihistamines.

WO 03/049770 discloses compositions and methods for treating rhinitis with H1 antagonists/antiallergics and safe steroids.

U.S. Pat. No. 5,164,194 is related to nasal formulations for azelastine.

DETAILED DESCRIPTION OF THE INVENTION

Surprisingly it has now been found that combined administration of ciclesonide and at least one antihistamine results in a very effective and safe treatment of symptoms accompanied with allergic rhinitis and/or allergic conjunctivitis. In particular by combined administration of the ciclesonide and the antihistamine as hypotonic aqueous pharmaceutical formulation a rapid onset of action and quick symptom relief is observed without the fear of glucocorticoid like side effects. By administering such hypotonic aqueous pharmaceutical composition according to the invention to the nasal mucosa the active ingredients rapidly enter the nasal mucosa and have a very long retention time. Therefore very low doses of ciclesonide and a once-daily, maximal twice-daily treatment is necessary to achieve an effective treatment.

In one aspect the present invention therefore relates to the combined administration of ciclesonide and at least one antihistamine for the treatment of allergic rhinitis and/or allergic conjunctivitis. Another subject of the invention therefore is a pharmaceutical composition for the treatment of allergic rhinitis and/or allergic conjunctivitis comprising as active ingredients a combination of at least one antihistamine, a pharmaceutically acceptable salt and/or a solvate or physiologically functional derivative thereof and ciclesonide, pharmaceutically acceptable salts of ciclesonide, epimers of ciclesonide in any mixing ratio with ciclesonide, solvates of ciclesonide, physiologically functional derivatives of ciclesonide or solvates thereof and a pharmaceutically acceptable carrier and/or one or more excipients.

It will be appreciated that the compounds of the combination may be administered simultaneously, either in the same pharmaceutical formulation (hereinafter also referred to as fixed combination) or in different pharmaceutical formulations (hereinafter also referred to as free combination) or sequentially in any order. If there is sequential administration, the delay in administering the second compound should not be such as to lose the beneficial therapeutic effect of the combination. As an example, both drugs may be provided separately as oral formulations, or one may be an oral preparation and the other an inhalant, or both may be provided in a form suitable for application to mucosa (nasal application).

Administration may be at the same time. Or they may be administered either close in time or remotely, such as where one drug is administered in the morning and the second drug is administered in the evening.

Accordingly, the present invention also provides a method for the prophylaxis or treatment of allergic rhinitis and/or allergic conjunctivitis in a mammal, such as a human, which comprises administration of a therapeutically effective amount of a pharmaceutical formulation comprising at least one antihistamine or a pharmaceutical acceptable salt, solvate, or physiologically functional derivative thereof and ciclesonide or a pharmaceutical acceptable salt, solvate, or physiologically functional derivative thereof, and a pharmaceutical acceptable carrier and/or one or more excipients. In a preferred aspect, there is provided such a method, which comprises administration of a therapeutically effective amount of a combination comprising at least one antihistamine and ciclesonide, and a pharmaceutical acceptable carrier and/or one or more excipients.

The formulations include those suitable for oral, parenteral including subcutaneous, intradermal, intramuscular, intravenous and intraaarticular, intranasal, inhalation (including fine particle dusts or mists which may be generated by means of various types of metered dose pressurised aerosols, nebulisers or insufflators), rectal and topical (including dermal, buccal, sublingual and intraocular administration) although the most suitable route may depend upon for example the condition and disorder of the recipient. In a preferred embodiment according to the invention the formulation is suitable for topical administration. In a preferred embodiment the formulation according to the invention is a formulation suitable for application to mucosa in the case of treatment of allergic rhinitis. In the case of treatment of allergic conjunctivitis a preferred formulation is a formulation suitable for conjunctival administration (application to the conjunctival sac). The formulations may conveniently be presented in unit dosage form and may be prepared by any of the methods well known in the art of pharmacy. All methods include the step of bringing the active ingredients into association with the carrier, which constitutes one or more accessory ingredients/excipients. In general the formulations are prepared by uniformly and intimately bringing into association the active ingredients with liquid carriers or finely divided solid carriers or both and then, if necessary, shaping the product into the desired formulation.

In a preferred embodiment the present invention relates to an aqueous pharmaceutical composition for the treatment of allergic rhinitis for application to the mucosa, comprising as active ingredients a combination of at least one antihistamine and ciclesonide. In particular the aqueous pharmaceutical composition is a sterile aqueous pharmaceutical composition.

The present invention further relates to an aqueous pharmaceutical composition for the treatment of allergic rhinitis for application to the mucosa comprising as active ingredients a combination of at least one antihistamine and ciclesonide together with one or more water-insoluble and/or water-low soluble substance and having an osmotic pressure of less than 290 mOsm. Preferably the osmotic pressure is 150 mOsm or lower, more preferably 72 mOsm or lower, more preferably 60 mOsm or lower, more preferably 40 mOsm or lower, more preferably 30 mOsm or lower and still more preferably 20 mOsm (e.g. 10 mOsm or lower).

According to the present invention it is not particularly required to add a substance for controlling osmotic pressure (osmotic pressure-controlling agent) but when it is added any substance can be used. In the present invention, a substance for controlling osmotic pressure (osmotic pressure controlling agent) can be added to control osmotic pressure, specific examples of which include salts such as sodium chloride and water-soluble sugars such as glucose, with glucose being a particularly preferable example.

In a preferred embodiment the pharmaceutical composition is a pharmaceutical composition as described for ciclesonide in WO 01/28562 or WO 01/28563.

Thus in one aspect the present invention relates to an aqueous pharmaceutical composition for the treatment of allergic rhinitis for application to the mucosa, comprising as active ingredients a combination of at least one antihistamine and ciclesonide together with one or more water-insoluble and/or water-low soluble substance and having an osmotic pressure of less than 290 mOsm.

The water-insoluble or water-low soluble substance may be any substance, and preferred examples include celluloses, more preferably crystalline celluloses and particularly preferred microcrystalline celluloses. According to the present invention, the concentration of water-insoluble and/or water-low soluble substance present in form of solid particles in an aqueous medium is preferably 0.3% w/w and above, and particularly preferably 0.5% w/w to 5% w/w, relative to the total amount of the composition.

In addition, an aqueous polymer substance can also be added in the present pharmaceutical composition. Specific examples of such include propylene glycol alginate, pectin, low methoxyl pectin, gua gum, gum Arabic, carrageenan, methyl cellulose, carboxymethyl cellulose sodium, xanthan gum hydroxypropylmethyl cellulose and hydroxypropyl cellulose, while particularly preferable examples include carboxymethyl cellulose sodium, polyethylene glycol and hydroxypropyl cellulose. Carboxymethyl cellulose sodium blended with microcrystalline cellulose, is an example of a combination of these water-soluble substance and water-insoluble substance that can be used in the present invention. Furthermore, in the case of adding these water-soluble polymer substances, the concentration of said substance is preferably 1% w/w to 30% w/w relative to the water-insoluble substance and/or water-low soluble substance.

In a preferred embodiment of the invention hydroxypropylmethyl cellulose is contained in the pharmaceutical compositions according to the invention. The hydroxypropylmethyl cellulose may be any grade, a specific example is hydroxypropylmethyl cellulose 2910. Although said hydroxypropylmethyl cellulose may be present at any concentration, its concentration is preferably from 0.001% w/w to 30% w/w, particularly preferably form 0.01% w/w to 5% w/w, more particularly preferably from 0.01% w/w to 1% w/w, and most preferably from 0.01% w/w to 0.5% w/w, relative to the total amount of composition.

A surfactant and/or wetting agent, although not essential in the present invention, can be added, specific examples of which include Polysorbate 80, glycerin monosterarate, polyoxyl stearate, lauromacrogol, sorbitan oleate and sucrose fatty acid esters.

An effective amount of ciclesonide and the topical antihistamine used in the present invention can be determined according to the type and degree of the respective disease, as well as the age and body weight of the patient, and so forth. Preferably the pharmaceutical composition according to the invention is administered as one to four sprays per nostril once or twice a day. The dose of ciclesonide per actuation is expediently from 10 μg to 400 μg, preferably 20 μg to 200 μg. The dose of the antihistamine per actuation will depend on the type of antihistamine and the route of administration. Expediently the dose is from 10 μg to 500 μg, preferably 25 μg to 250 µg per actuation. In case of azelastin the dose preferably is within the ranges described in U.S. Pat. No. 5,164,194.

Ciclesonide (hereinafter also referred to as active ingredient) is the INN for a compound with the chemical name [11β, 16α(R)]-16,17-[(Cyclohexylmethylen)bis(oxy)]-11-hydroxy-21-(2-methyl-1-oxopropoxy)pregna-1,4-dien-3,20-dion. Ciclesonide and its preparation are disclosed in DE 4129535. Ciclesonide as used herein also includes, pharmaceutically acceptable salts of ciclesonide, epimers of ciclesonide (e.g. [11β, 16α(S)]-16,17-[(Cyclohexylmethylen)bis(oxy)]-11-hydroxy-21-(2-methyl-1-oxopropoxy)-pregna-1,4-dien-3,20-dion) in any mixing ratio with ciclesonide, solvates of ciclesonide, physiologically functional derivatives of ciclesonide or solvates thereof. By the term "physiologically functional derivative" is meant a chemical derivative of ciclesonide having the same physiological function as ciclesonide, for example, by being convertible in the body thereto or by being an active metabolite of ciclesonide. Physiological functional derivatives of ciclesonide which may be mentioned in connection with the invention are for example the 21-hydroxy derivative of ciclesonide with the chemical name 16α, 17-(22R,S)-Cyclohexylmethylendioxy-11β,21-dihydroxypregna-1,4-dien-3, 20-dion, 16α, 17-(22S)-Cyclohexylmethylendioxy-11β,21-dihydroxypregna-1,4-dien-3,20-dion and in particular 16α, 17-(22R)-Cyclohexylmethylendioxy-11β,21-dihydroxypregna-1,4-dien-3,20-dion. This compound and its preparation are disclosed in WO 9422899.

Preferably ciclesonide is dispersed in the aqueous medium in form of solid particles.

The concentration of ciclesonide of the present invention is preferably from 0.01% w/w to 1% w/w, and particularly preferably from 0.05 w/w to 0.5% w/w, relative to the total amount of the composition.

Although the ciclesonide particles that can be used in the present invention may be of any size, they are preferably within the range of 10 nm to 100 µm, and particularly preferably within the range of 100 nm to 10 µm.

Antihistamines, which may be mentioned in connection with the invention, can be any antihistamine suitable for the treatment of allergic rhinitis and/or allergic conjunctivitis. Examples which may be mentioned are (E)-6-[(E)-3-(1-pyrrolidinyl)-1-p-tolylpropenyl]-2-pyridineacrylic acid [INN: ACRIVASTINE], 6,11-Dihydro-11-(1-methyl-4-piperidyliden)-5H-benzo[5,6]cyclohepta-[1,2-b]pyridin [INN: AZATADINE], 4-[(4-chlorophenyl)methyl]-2-(hexahydro-1-methyl-1H-azepin-4-yl)-1(2H)phthalazinone [INN: AZELASTINE], (+)-(S)-4-[4-[1-(4-chlorophenyl)-1-(2-pyridyl)methoxy]piperidin-1-yl]-butanoic acid [INN: BEPOTASTINE], (plus/minus)-[2-[4-(p-chloro-alpha-phenylbenzyl)-1-piperazinyl]ethoxy]-acetic acid [INN: CETIRIZINE], (+)-2-{2-[(p-Chlor-alpha-methyl-alpha phenylbenzyl)oxy]ethyl}-1-methylpyrrolidin [INN: CLEMASTINE], 8-chloro-6,11-dihydro-11-(4-piperidylidene)-5H-benzo[5,6]cyclohepta-[1,2-b]pyridine [INN: DESLORATADINE], [3-(4-Chlorophenyl)-3-pyridin-2-yl-propyl]-dimethylamine [INN: DEXCHLORPHENIRAMINE], 4'-tert-butyl-4-[4-(diphenylmethoxy)piperidino]butyrophenone [INN: EBASTINE], [2-[4-[bis(p-fluorophenyl)methyl]-1-piperazinyl]ethoxy] acetic acid [INN: EFLETIRIZINE], 1-(2-ethoxyethyl)-2-(hexahydro-4-methyl-1H-1,4-diazepin-1-yl)-benzimidazole [INN: EMEDASTINE], 3-amino-9,13b-di-hydro-1H-dibenz[c,f]imidazo[1,5-a]azepine [INN: EPINASTINE], (plus/minus)-p-[1-hydroxy-4-[4-(hydro-xydiphenylmethyl)piperidino]-butyl]-alpha-methylhydratropic acid [INN: FEXOFENADINE], 3-[4-(8-fluoro-5,11-dihydrobenz[b]oxepino[4,3-b]pyridin-11-ylidene)-piperidin-1-yl]propionic acid [Research Code: HSR-609], (−)-(3S,4R)-1-[cis-4-cyano-4-(p-fluorophenyl)cyclohexyl]-3-methyl-4-phenyl-isonipecotic acid [INN: LEVOCABASTINE], [2-[4-[(R)-p-chloro-alpha-phenylbenzyl)-1-piperazinyl]ethoxy]-acetic acid [INN: LEVOCETIRIZINE], ethyl 4-(8-chloro-5,6-dihydro-11H-benzo[5,6]cyclohepta[1,2-b]pyridin-11-ylidene)-1-piperidinecarboxylate [INN: LORATADINE], 2-[N-[1-(4-fluorobenzyl)-1H-benzimidazol-2-yl]-4-piperidinyl]-N-methyl-amino]pyrimidin-4(3H)-one [INN: MIZOLASTINE], 1-(4-fluorobenzyl)-2-(piperidin-4-ylamino)-1H-benzimidazole [INN: NORASTEMIZOLE], 3-(10,11-dihydro-5H-dibenzo[a,d]cyclohepten-5-ylidene)-N-methyl-1-propanamine [INN: NORTRIPTYLINE], 9-methyl-3-(1H-tetrazol-5-yl)-4H-pyrido[1,2-a]pyrimidin-4-one [INN: PEMIROLAST], 8-chloro-11-[1-(5-methylpyridin-3-ylmethyl)piperidin-4-yl-idene)-6,11-dihydro-5H-benzo[5,6]cyclohepta[1,2-b]pyridine [INN: RUPATADINE], 1-[2-[(p-chloro-alpha-methyl-alpha-phenylbenzyl)oxy]ethyl] hexahydro-1H-azepine [INN: SETASTINE], S-(7-carboxy-4-hexyl-9-oxoxanthen-2-yl)-S-methylsulfoximine [INN: SUDEXANOX], 1-(p-tert-butylphenyl)-4-[4'-(alpha-hydroxydiphenylmethyl)-1'-piperidyl]-butanol [INN: TERFENADINE], N-benzyl-N,N'-dimethyl-N-(2-pyridyl)-ethylenediamine [INN: TRIPELENAMINE] and 1-(4-fluorobenzyl)-2-(piperidin-4-ylamino)-1H-benzimidazole [INN: TECASTEMIZOLE] and mixtures thereof. The antihistamine may also be present in form of a pharmaceutically acceptable salt and/or a solvate. Depending on the chemical structure the antihistamine may exist in different stereoisomeric forms. The term antihistamine includes the pure stereoisomers (eg. pure epimer, diastereoisomer or enantiomer) and their mixtures in any mixing ratio. Suitable pharmacologically acceptable salts of antihistamines are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methane-sulfonic acid or 1-hydroxy-2-naphthoic acid, the acids being employed in salt preparation— depending on whether it is a mono- or polybasic acid and depending on which salt is desired—in an equimolar quantitative ratio or one differing therefrom. By the term "physiologically functional derivative" is meant a chemical derivative of an antihistamine having the same physiological function as the antihistamine, for example, by being convertible in the body thereto or by being an active metabolite of the antihistamine. In a preferred embodiment the antihistamine is an antihistamine with long acting topical activity. Azatadine, azelastin, levocabastin and pharmaceutically acceptable salts thereof are particularly preferred. Azatadine is known e.g. from U.S. Pat. No. 3,326,924. Preferred salts of azatadine include its maleate, sulfate, succinate and acetate salts. Azelastine is known from U.S. Pat. No. 3,813,384 and from U.S. Pat. No. 5,164,194. Preferred are acid addition salts, such as, the hydrohalogen salt and salts with organic acids. Preferred salts include the hydrochloride, hydrobromide, salts with embonic acid, maleic acid, citric acid and tartaric acid. Levocabastine is known from U.S. Pat. No. 4,369,184. Suitable salts include the hydrochloride, hydrobromide and salts with sulphuric acid, nitric acid, acetic acid and propionic acid.

In case of water soluble antihistamines such as azelastin hydrochloride, the antihistamine will be dissolved in the pharmaceutical compositions according to the invention.

The concentration of the topical antihistamine is preferably from 0.01% w/w to 0.5% w/w, and particularly preferably from 0.05 w/w to 0.2% w/w, relative to the total amount of the composition.

Any method for dispersing a water-insoluble substance and/or water-low soluble substance in an aqueous medium may be used for the production of the aqueous pharmaceutical composition according to the invention, a specific example of which is a method that uses a homomixer.

Known antiseptics, pH controlling agents, preservatives, buffers, colorants, smell corrigents and so forth may be added as necessary to the compositions of the present invention to improve its physical properties, stability, appearance or odor and so forth of the formulation.

Examples of antiseptics include benzalkonium chloride, examples of pH controlling agents include hydrochloric acid and sodium hydroxide, examples of preservatives include potassium sorbate, examples of buffers include phosphoric acid and its salt, examples of colorants include red dye no. 2, and examples of smell corrigents include menthol.

Due to the unique galenic formulation, ciclesonide rapidly enters the nasal mucosa and has a very long retention time. Therefore, very low doses of ciclesonide and the once daily, maximal twice-daily treatment is necessary to achieve an effective treatment. A low dose of ciclesonide in a hypotonic watery suspension in combination with a topical antihistamine (e.g. azelastine or levocabastine) results in a very effective and safe treatment of all symptoms accompanied with allergic rhinitis. A clear advantage of this combination is the rapid onset of action and quick symptom relief without the fear of glucocorticoid like side effects.

In another embodiment the present invention relates to a combination of ciclesonide with azelasine and ciclesonide is applied in a pharmaceutical composition as described for ciclesonide in WO 01/28562 or WO 01/28563 and azelastine is applied in a pharmaceutical formulation according to U.S. Pat. No. 5,164,194.

When given to the nasal mucosa the formulation according to the present invention may be filled into plastic squeeze bottles or plastic or glass bottles, which are fitted with a metering atomising pump and a nasal adapter or with a suitable dropper. When given to the eye the formulation according to the present invention may be filled into plastic squeeze bottles or plastic or glass bottles, which are fitted with a suitable dropper.

EXAMPLES

Ciclesonide aqueous pharmaceutical compositons containing the components indicated below are prepared by processing with a homomixer. Homomixer processing is performed, e.g., at 6000 rpm for 30 minutes.

Example 1

Combination of Ciclesonide and Azelastine Hydrochloride

| | |
|---|---|
| Ciclesonide: | 0.05% |
| Azelastine hydrochloride | 0.14% |
| Microcrystalline cellulose and carboxymethyl cellulose sodium | 1.7% |
| Hydroxypropylmethyl cellulose 2910 | 0.1% |

Each 100 mg spray delivered by a nasal applicator delivers 50 μg of ciclesonide and 140 μg of azelastine hydrochloride.

Example 2

Combination of Ciclesonide and Levocabastine Hydrochloride

| | |
|---|---|
| Ciclesonide: | 0.05% |
| Levocabastine hydrochloride | 0.054% |
| Microcrystalline cellulose and carboxymethyl cellulose sodium | 1.7% |
| Hydroxypropylmethyl cellulose 2910 | 0.1% |

Each 100 mg spray delivered by a nasal applicator delivers 50 μg of ciclesonide and 54 μg of levocabastine hydrochloride (equivalent to 50 μg levocabastine).

The invention claimed is:

1. A method for the treatment of allergic rhinitis and/or allergic conjunctivitis in a patient, comprising administering to a patient in need thereof a therapeutically effective amount of a pharmaceutical composition comprising, as sole active ingredients, a combination of
   at least one antihistamine, a stereoisomer, a pharmaceutically acceptable salt, thereof, and
   ciclesonide, pharmaceutically acceptable salts of ciclesonide, or epimers of ciclesonide optionally in any mixing ratio with ciclesonide
   and a pharmaceutically acceptable carrier and/or one or more excipients, wherein the pharmaceutical composition is administered as one to four sprays per nostril once or twice a day, and wherein the dose of ciclesonide per actuation is 10μg to 400μg and the dose of antihistamine per actuation is 10μg to 500μg.

2. The method of claim 1, wherein said patient is a human.

3. The method according to claim 1, wherein the pharmaceutical composition is an aqueous pharmaceutical composition comprising the active ingredients together with one or more water-insoluble and/or water-low soluble substances, and wherein said pharmaceutical composition has an osmotic pressure of less than 290 mOsm.

4. The method according to claim 2, wherein said pharmaceutical composition has an osmotic pressure of 150 mOsm or less.

5. The method according to claim 2, wherein said pharmaceutical composition has an osmotic pressure of 60 mOsm or less.

6. The method according to claim 2, wherein said pharmaceutical composition has an osmotic pressure of 40 mOsm or less.

7. The method according to claim 2, wherein said pharmaceutical composition has an osmotic pressure of 20 mOsm or less.

8. The method according to claim 2, wherein said pharmaceutical composition further comprises an osmotic pressure-controlling agent.

9. The method according to claim 2, wherein said water-insoluble and/or water-low soluble substance is a cellulose.

10. The method according to claim 9, wherein said cellulose is microcrystalline cellulose.

11. The method according to claim 2, wherein said one or more water-insoluble and/or water-low soluble substances is/are present as solid particles in an aqueous medium.

12. The method according to claim 2, wherein said pharmaceutical composition further comprises a water-soluble polymer substance.

13. The method according to claim 12, wherein a combination of said water-insoluble substance and water-soluble polymer is present which is microcrystalline cellulose and carboxymethyl cellulose sodium.

14. The method according to claim 2, wherein said pharmaceutical composition further comprises a surfactant and/or a wetting agent.

15. The method according to claim 1, wherein the antihistamine is selected from the group consisting of (E)-6-[(E)-3-(1-pyrrolidinyl)-1-p-tolylpropenyl]-2-pyridineacrylic acid (ACRIVASTINE), 6,11-Dihydro-11-(1-methyl-4-piperidyliden)-5H-benzo[5,6]cyclohepta-[1,2-b]pyridine (AZATADINE), 4-[(4-chlorophenyl)methyl]-2-(hexahydro-1-methyl-1H-azepin-4-yl)-1(2H)phthalazinone (AZELASTINE), (+)-(S)-4-[4-[1-(4-chlorophenyl)-1-(2-pyridyl)methoxy]piperidin-1-yl]-butanoic acid (BEPOTASTINE), (+/+)-[2-[4-(p-chloro-alpha-phenylbenzyl)-1-piperazinyl]ethoxy]-acetic acid (CETIRIZINE), (+)-2-{2-[(p-Chlor-alpha-methyl-alpha phenylbenzyl)oxy]-ethyl}-1-methylpyrrolidin (CLEMASTINE), 8-chloro-6,11-dihydro-11-(4-piperidylidene-5H-benzo[5,6]-cyclohepta-[1,2-b]pyridine (DESLORATADINE), [3-(4-Chlorophenyl)-3-pyridin-2-yl-propyl]-dimethylamine (DEXCHLORPHENIRAMINE), 4'-tert-butyl-4-[4-(diphenylmethoxy)-piperidino]butyrophenone (EBASTINE), [2-[4-[bis(p-fluorophenyl)methyl]-1-piperazinyl]ethoxy]-acetic acid (EFLETIRIZINE), 1-(2-ethoxyethyl)-2-hexahydro-4-methyl-1H-1,4-diazepin-1-ylybenzimidazole (EMEDASTINE), 3-amino-9,13b-dihydro-1H-dibenz[c,f]imidazo[1,5-a]azepine (EPINASTINE), (+/−)-p-[1-hydroxy-4-[4-(hydroxydiphenylmethyl)piperidino]-butyl]-alpha-methylhydratropic acid (FEXOFENADINE), 3-[4-(8-fluoro-5,11-dihydrobenz[b] oxepino[4,3-b]pyridin-11-ylidene)-piperidin-1-yl]propionic acid (Research Code HSR-609), (−)-(3S,4R)-1-[cis-4-cyano-4-(p-fluorophenyl)cyclohexyl]-3-methyl-4-phenylisonipecotic acid (LEVOCABASTINE), [2-[4-[(R)-p-chloro-alpha-phenylbenzyl)-1-piperazinyl]ethoxy]-acetic acid (LEVOCETIRIZINE), ethyl 4-(8-chloro-5,6-dihydro-11H-benzo[5,6]cyclohepta[1,2-b]pyridin-11-ylidene)-1-piperidinecarboxylate (LORATADINE), 2-[N-[1-(4-fluorobenzyl)-1H-benzimidazol-2-yl]-4-piperidinyl]-N-methyl-amino] pyrimidin-4(3H)-one (MIZOLASTINE), 1-(4-fluorobenzyl)-2-(piperidin-4-ylamino)-1H-benzimidazole (NORASTMIZOLE), 3-(10,11-dihydro-5H-dibenzo[a,d]cyclo-hepten-5-ylidene)-N-methyl-1-propanamine (NORTRIPTYLINE), 9-methyl-3-(1H-tetrazol-5-yl)-4H-pyrido[1,2-a]pyrimidin-4-one (PEMIROLAST), 8-chloro-11-[1-(5-methylpyridin-3-ylmethyl)-piperidin-4-ylidene]-6,11-dihydro-5H-benzo[5,6]cyclohepta[1,2-b]pyridine (RUPATADINE), 1-[2-[(p-chloro-alpha-methyl-alpha-phenylbenzyl)-oxy]ethyl]hexahydro-1H-azepine (SETASTINE), S-(7-carboxy-4-hexyl-9-oxoxanthen-2-yl)-S-methylsulfoximine (SUDEXANOX), 1-(p-tert-butyl-phenyl)-4-[4'-(alpha-hydroxydiphenylmethyl)-t-piperidyl]-butanol (TERFENADINE), N-benzyl-N,N'-dimethyl-N-(2-pyridyl)-ethylenediamine (TRIPELENAMINE), 1-(4-fluorobenzyl)-2-(piperidin-4-ylamino)-1H-benzimidazole (TECASTEMIZOLE), stereoisomers thereof, pharmaceutically acceptable salts thereof, and mixtures thereof.

16. The method according to claim 1, wherein the antihistamine is selected from the group consisting of azelastine, levocabastine, and pharmaceutically acceptable salts thereof.

17. The method according to claim 1, wherein said epimer of ciclesonide is [11β,16α(S)]-16,17-[(cyclohexylmethylen) bis(oxy)]-11-hydroxy-21-(2-methyl-1-oxopropoxy)-pregna-1,4-dien-3,20-dion and is present in any mixing ratio with ciclesonide, [11β,16α(R)]-16,17-[(cyclohexylmethylen)bis (oxy)]-11-hydroxy-21-(2-methyl-1-oxopropoxy)-pregna-1, 4-dien-3,20-dion.

* * * * *

UNITED STATES PATENT AND TRADEMARK OFFICE
CERTIFICATE OF CORRECTION

PATENT NO. : 8,486,923 B2  
APPLICATION NO. : 12/973414  
DATED : July 16, 2013  
INVENTOR(S) : Marx et al.

Page 1 of 2

It is certified that error appears in the above-identified patent and that said Letters Patent is hereby corrected as shown below:

In the Claims:

Claim 1, Col. 8, line 28, "stereoisomer, a" should read -- stereoisomer, or a --

Claim 1, Col. 8, line 29, "salt, thereof, and" should read -- salt thereof, and --

Claim 1, Col. 8, line 32, "with ciclesonide" should read -- with ciclesonide, --

Claim 4, Col. 8, lines 46-48 should read as follows:

-- The method according to claim 3, wherein said pharmaceutical composition has an osmotic pressure of 150 mOsm or less. --

Claim 5, Col. 8, lines 49-51 should read as follows:

-- The method according to claim 3, wherein said pharmaceutical composition has an osmotic pressure of 60 mOsm or less. --

Claim 6, Col. 8, lines 52-54 should read as follows:

-- The method according to claim 3, wherein said pharmaceutical composition has an osmotic pressure of 40 mOsm or less. --

Claim 7, Col. 8, lines 55-57 should read as follows:

-- The method according to claim 3, wherein said pharmaceutical composition has an osmotic pressure of 20 mOsm or less. --

Signed and Sealed this  
Fifteenth Day of October, 2013

Teresa Stanek Rea  
*Deputy Director of the United States Patent and Trademark Office*

CERTIFICATE OF CORRECTION (continued)
U.S. Pat. No. 8,486,923 B2

Claim 8, Col. 8, lines 58-60 should read as follows:

-- The method according to claim 3, wherein said pharmaceutical composition further comprises an osmotic pressure-controlling agent. --

Claim 9, Col. 8, lines 61-62 should read as follows:

-- The method according to claim 3, wherein said water-insoluble and/or water-low soluble substance is a cellulose. --

Claim 11, Col. 8, lines 65-67 should read as follows:

-- The method according to claim 3, wherein said one or more water-insoluble and/or water-low soluble substances is/are present as solid particles in an aqueous medium. --

Claim 12, Col. 9, lines 1-3 should read as follows:

-- The method according to claim 3, wherein said pharmaceutical composition further comprises a water-soluble polymer substance. --

Claim 14, Col. 9, lines 8-10 should read as follows:

-- The method according to claim 3, wherein said pharmaceutical composition further comprises a surfactant and/or a wetting agent. --

Claim 15, Col. 9, line 19, "(+/+)" should read -- (+/-) --

Claim 15, Col. 9, line 31, "ylybenzimidazole" should read -- yl)benzimidazole --

Claim 15, Col 10, line 21, "(alpha-hydroxydiphenylmethyl)-t-piperidyl]-butanol" should read -- (alpha-hydroxydiphenylmethyl)-1'-piperidyl]-butanol --